United States Patent [19]

Suganuma et al.

[11] Patent Number: 4,980,489
[45] Date of Patent: Dec. 25, 1990

[54] 2-(1-ALKYLAMINOALKYL)-3-HYDROXY-1,4-NAPHTHOQUINONE

[75] Inventors: Hiroyuki Suganuma; Hiroshi Fujimura, both of Kawasaki, Japan

[73] Assignee: Kawasaki Kasei Chemicals Ltd., Tokyo, Japan

[21] Appl. No.: 310,623

[22] Filed: Feb. 15, 1989

[30] Foreign Application Priority Data

Feb. 23, 1988 [JP] Japan ................................. 63-41755
May 12, 1988 [JP] Japan ................................. 63-115055

[51] Int. Cl.$^5$ .......................................... C07C 225/24
[52] U.S. Cl. ............................................. 552/298.000
[58] Field of Search .................................... 552/298

[56] References Cited

U.S. PATENT DOCUMENTS 2,541,473 2/1951 Leffler ................................. 552/298
2,553,647 5/1951 Fieser et al. ......................... 552/298
4,110,473 8/1978 Fugitt et al. ..................... 552/298 X

FOREIGN PATENT DOCUMENTS 2520739 11/1975 Fed. Rep. of Germany .
2323676 4/1977 France .

OTHER PUBLICATIONS

Journal of the Amer. Chem. Society, vol. 71, May, 1949, pp. 1697–1702; C. E. Dalgliesh: "Naphthoquinone Antimaterials. Mannich Bases Derived from Lawsone".
Journal of the Chem. Society, Perkin Transactions I, 1986, pp. 659–664; K. Bock et al., "Reaction of 2-Hydroxy-1,4-naphthoquinone with aldehydes. Synthesis of 2-Hydroxy-3-alk-1-enylnaphthoquinones".
Journal of the Amer. Chem. Society, vol. 58, Jul., 1936, pp. 1163–1167; S. C. Hooker: "Condensation of Aldehydes with Beta-Hydroxy-alpha-naphthoquinone, Synthesis of Hydrolapachol".
Chemical Abstracts, vol. 94, No. 23, Jun. 8, 1981, p. 625, Column 2, Abstract No. 191985y, Columbus, Oh.,
G.-L. XI et al.; "Studies on Antiasthmatic Agents, II. Synthesis of some Omega-(e-hydroxyl-1,4-naphthoquinonyl-2)-alkanoic acids and Mannich bases of 2-hydroxy-1,4-naphthoquinone"& Yao Hsueh Hsueh Pao 1980, vol. 15, No. 9, pp. 548–554.
Chemical Abstracts, vol. 78, No. 7, Feb., 1973, p. 549, column 2, Abstract No. 43130v, Columbus, Oh., U.S.A.; JP-A-72 029353.
Leffler, M. T. et al., J. Amer. Chem. Soc., 70, 3222 (1948).
Dalglish, C. E., J. Amer. Chem. Soc., 71, 1697 (1944).
Fieser, L. T. et al. J. Am. Chem. Soc., 70, 3156 (1948).

Primary Examiner—Vivian Garner
Attorney, Agent, or Firm—Oblon, Spivak, McClelland, Maier & Neustadt

[57] ABSTRACT

A 2-(1-alkylaminoalkyl)-3-hydroxy-1,4-naphthoquinone of the formula:

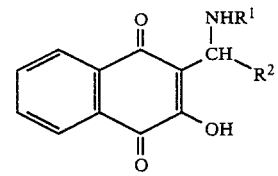

wherein $R^1$ is an alkyl group or a cycloalkyl group, and $R^2$ is an alkyl group having at least 2 carbon atoms.

The compounds are used in the preparation of a 2-(1-alkenyl)-3-hydroxy-1,4-naphthoquinone having insecticidal and fungicidal activity and a 2-alkyl-3-acyloxy-1,4-naphthoquinone having insecticidal and fungicidal activity and a 2-alkyl-3-acyloxy-1,4-naphthoquinone having miticidal activity.

10 Claims, No Drawings

2-(1-ALKYLAMINOALKYL)-3-HYDROXY-1,4-NAPHTHOQUINONE

The present invention relates to a novel 2-(1-alkylaminoalkyl)-3-hydroxy-1,4-naphthoquinone and a process for producing it, as well as processes for producing a 2-(1-alkenyl)-3-hydroxy-1,4-naphthoquinone and a 2-alkyl-3-acyloxy-1,4-naphthoquinone, by means of the novel compound.

A 2 (1-alkenyl)-3-hydroxy-1,4-naphthoquinone is a compound having insecticidal and fungicidal activities. Further, a 2-alkyl-3-hydroxy-1,4-naphthoquinone obtained by the hydrogenation of the alkenyl group, is useful as medicines, animal drugs and agricultural chemicals.

The 2-alkyl 3-acyloxy-1,4-naphthoquinone is known as a compound having miticidal activities (see, for example, Japanese Unexamined Patent Publications No. 155620/1975 and No. 48648/1977). A 2-(1-alkenyl)-3-hydroxy-1,4-naphthoquinone as its intermediate and a 2-alkyl-3-hydroxy-1,4-naphthoquinone as its hydrogenated product are useful as medicines, animal drugs and agricultural chemicals.

Heretofore, it is known that a 2-alkylaminomethyl-3-hydroxy-1,4-naphthoquinone can readily be obtained by reacting 2-hydroxy-1,4-naphthoquinone with formalin and a primary or secondary amine (M. T. Leffler and R. J. Hathaway: J. Amer. Chem. Soc., 70, 3222 (1948)). Further, it is known that by the reaction with benzaldehyde or acetaldehyde, it gives a 2-(1-alkylaminobenzyl)-3-hydroxy-1,4-naphthoquinone or a 2-(1-alkylaminoethyl)-3-hydroxy-1,4-naphthoquinone (C. E. Dalgliesh: J. Amer. Chem. Soc., 71, 1697 (1944)). Further, it is known that these compounds have antimalaria activities (L. F. Fieser and A. R. Richardson: J. Amer. Chem. Soc., 70, 3156 (1948)). On the other hand, for the preparation of a 2 (1-alkenyl)-3-hydroxy-1,4-naphthoquinone, only the following methods are known:

(1) A method wherein 2-hydroxy-1,4 naphthoquinone and a few mol times of an aldehyde are subjected to dehydration condensation in an acetic acid solvent in the presence of about 1.7 mol times of hydrochloric acid as catalyst (Samuel C. Hooker: J. Am. Chem. Soc., 58, p. 1163–1167 (1936)); and (2) A method which is the same as the method (1) except that triethylamine is used as catalyst instead of hydrochloric acid, and dimethylformamide or acetonitrile is used as solvent (Klaus Bock, Niels Jacobsen and Buelent Terem: J. Chem. Soc. Perkin Trans. I, p. 659–664 (1986)).

For the production of a 2-alkyl-3-acyloxy-1,4-naphthoquinone, the following methods are known:

(3) A method in which a 4-phenylacetoacetic acid ester is used as starting material (U.S. Pat. No. 2,553,647);

(4) A method wherein u-naphthol is used as starting material (Japanese Unexamined Patent Publication No. 48648/1977, and U.S. Pat. No. 4,110,473);

(5) A method wherein 2,3-dichloro-1,4-naphthoquinone is used as starting material, and an organo metal compound is used as a reagent for reaction (U.S. Pat. No. 4,507,741); and (6) A method wherein 2-acyloxy-1,4-naphthoquinone is used as starting material, and an alkyl group is added thereto (Niels Jacobsen and Lars-Erik K. Pedersen, Pestic. Sci., 17, p. 511–516 (1986)).

Further, for the preparation of a 2-alkyl-3-hydroxy-1,4-naphthoquinone as a compound prior to the acyloxylation of the above compound, the following methods are known:

(7) A method wherein an alkyl radical generated from a diacyl peroxide is added to 2-hydroxy-1,4-naphthoquinone (L. F. Fieser, M. T. Leffler and Co-workers, J. Amer. Chem. Soc., 70, 3174 (1948)); and 8) A method wherein the 2-(1 alkenyl)-3-hydroxy-1,4-naphthoquinone obtained by the method (1) is hydrogenated and oxidized (Samuel C. Fooker, J. Amer. Chem. Soc., 58, 1163–1167 (1936)).

However, in the above-mentioned reports concerning the preparation of a 2-(1-alkylaminoalkyl)-3-hydroxy-1,4-naphthoquinone, it is reported that when an aldehyde other than formalin, benzaldehyde or acetoaldehyde is employed, the reaction does not proceed satisfactorily, and a tar-like substance will be formed, or a 2,2'-methylene-bis-3-hydroxy-1,4-naphthoquinone derivative will be formed, and when an aliphatic aldehyde having at least 3 carbon atoms is employed, the 2-(1-alkylaminoalkyl)-3-hydroxy-1,4-naphthoquinone is not obtained. Thus, the range of application of this reaction is limited.

Further, the above-mentioned methods for the production of a 2-(1-alkenyl)-3-hydroxy-1,4-naphthoquinone wherein hydrochloric acid is used as a catalyst, are not practically useful as industrial methods, since hydrochloric acid is extremely corrosive and the apparatus is required to be made of a special material. Besides, in each of such methods, the yield is only at a level of from 30 to 40 mol%, and yet a large excess of an aldehyde is used, whereby condensation products of the aldehyde or other by-products tend to form in large amounts, and the method of isolating the desired product tends to be cumbersome. Therefore, they are not industrially advantageous. The above-mentioned method (2) can not be commonly used, since in most cases, formation of a 2,2'-methylene-bis 3-hydroxy-1,4-naphthoquinone derivative proceeds preferentially.

The 2-alkyl-3-acyloxy-1,4-naphthoquinone was known to have high activities as an insecticide, particularly as a acaricide. Nevertheless, it has not been commercialized. The reason is that this compound is difficult to synthesize, and no method has been found which is industrially convenient and capable of producing the compound at a reasonable cost for its usefulness.

Namely, among the above-mentioned various methods, the methods (3) and (4) involve a number of process steps and require cumbersome operations, and therefore they are not suitable as industrial methods. In the methods (5) and (6), the starting materials or subsidiary materials are expensive, and the production costs tend to be expensive, although the process steps are short. In the methods (7) and (8), the yields are poor, and the operations are not industrial. Thus, none of them can be regarded as suitable for producing a 2-alkyl-3-acyloxy-1,4-naphthoquinone on an industrial scale at low costs.

It is an object of the present invention to provide a novel 2-(1-alkylaminoalkyl)-3-hydroxy-1,4-naphthoquinone and a process for its preparation.

Another object of the present invention is to provide a process for producing a 2-(1-alkenyl)-3-hydroxy-1,4-naphthoquinone from this novel compound.

A further object of the present invention is to overcome the above-mentioned drawbacks by using such compounds and processes and to provide a process whereby an inexpensive 2-alkyl-3 acyloxy-1,4-naphthoquinone useful as agricultural chemicals and its intermediate can be produced on an industrial scale.

The present inventors have conducted extensive researches for a process for producing a 2-(1-alkylaminoalkyl)-3-hydroxy-1,4-naphthoquinone and have found it possible to produce selectively and in high yield a novel 2-(1-alkylaminoalkyl) 3-hydroxy-1,4-naphthoquinone by using a primary amine and a certain specific solvent and by maintaining the reaction temperature at a level of not higher than 35° C., whereby various aldehydes other than formalin, benzaldehyde and acetoaldehyde, may be used. Further, it has been found that depending upon the solvent used, the product can readily be isolated as crystals. The first aspect of the present invention is based on these discoveries. Further, with respect to the production of a 2-(1-alkenyl) 3 hydroxy-1,4-naphthoquinone, it has been found possible to produce in good yield a 2-(1-alkenyl)-3-hydroxy-1,4-naphthoquinone by deaminating the 2-(1-alkylaminoalkyl)-3-hydroxy-1,4-naphthoquione obtained by the above mentioned process, in an inert organic solvent in the presence of an acid such as sulfuric acid or a hydrogen halide acid. Furthermore, it has been found that the 2-(1-alkylaminoalkyl)-3-hydroxy 1,4-naphthoquinone obtained by the process of the first aspect of the present invention, is suitable as a starting material for the preparation of a 2-alkyl-3-acyloxy-1,4-naphthoquinone, and that an intermediate obtainable during the process for its production, is also useful.

Namely, according to the first aspect, the present invention provides a novel 2-(1-alkylaminoalkyl)-3-hydroxy-1,4-naphthoquinone of the formula:

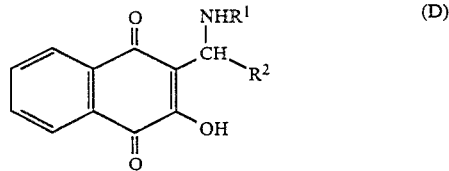

(D)

wherein $R^1$ is an alkyl group or a cycloalkyl group, and $R^2$ is an alkyl group having at least 2 carbon atoms, and a process for producing the 2-(1-alkylaminoalkyl) 3-hydroxy-1,4-naphthoquinone, which comprises reacting 2-hydroxy-1,4-naphthoquinone with an aliphatic aldehyde having at least 3 carbon atoms in an inert organic solvent in the presence of a primary amine.

According to the second aspect, the present invention provides a process for producing a 2 (1-alkenyl)-3-hydroxy-1,4-naphthoquinone, which comprises deaminating the novel 2-(1-alkylaminoalkyl)-3-hydroxy-1,4-naphthoquinone of the formula (D) in an inert organic solvent in the presence of an acid.

Further, in the third aspect, the present invention provides a process for producing a 2 alkyl-3 acyloxy-1,4-naphthoquinone, which comprises deaminating a 2-(1-alkylaminoalkyl)-3-hydroxy-1,4-naphthoquinone to form a 2-(1-alkenyl) 3 hydroxy-1,4-naphthoquinone, subjecting the product to hydrogenation to form a 2-alkyl-1,3,4-trihydroxynaphthalene, then subjecting this 2-alkyl-1,3,4-trihydroxynaphthalene to oxidation, and subjecting the resulting 2-alkyl-3-hydroxy-1,4-naphthoquinone to acyloxylation, whereby the 2-alkyl-3-acyloxy-1,4-naphthoquinone can be prepared in good yield at a low cost in an industrially convenient manner without using expensive raw materials.

Now, the present invention will be described in detail with reference to the preferred embodiments.

The novel naphthoquinone compound of the formula (D) can be obtained by reacting a 2-hydroxy-1,4-naphthoquinone (A) and an aliphatic aldehyde (B) having at least 3 carbon atoms in an inert organic solvent in the presence of a primary amine (C).

The reaction to obtain the 2 (1-alkylaminoalkyl)-3-hydroxy-1,4-naphthoquinone (D) by the above process may be represented by the following reaction scheme.

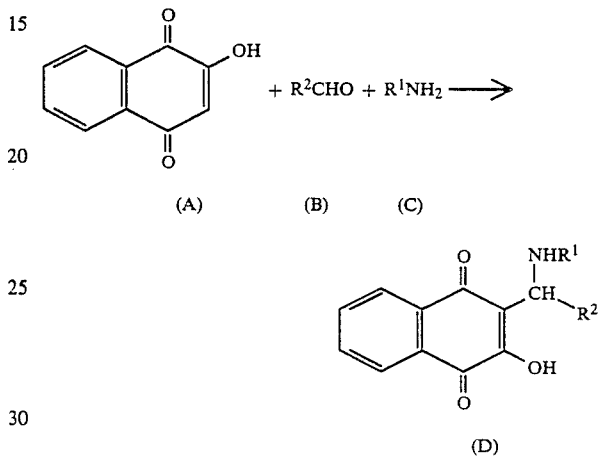

The aldehyde to be used in the present invention is an aldehyde having at least 3 carbon atoms and usually at most 21 carbon atoms, preferably from 5 to 20 carbon atoms, which may be represented by the formula $R^2CHO$, wherein $R^2$ is an alkyl group having from 2 to 20 carbon atoms, preferably from 4 to 19 carbon atoms. The aldehyde is selected depending upon $R^2$ of the desired compound (D).

Representative examples of the aldehyde include aliphatic saturated aldehydes such as propionaldehyde, butylaldehyde, isobutylaldehyde, valeraldehyde, isovaleraldehyde, pivalaldehyde, caproaldehyde, heptylaldehyde, caprylaldehyde, pelargonaldehyde, caprylaldehyde, undecylaldehyde, dodecylaldehyde (lauraldehyde), tridecylaldehyde, myristaldehyde, pentadecylaldehyde, margaraldehyde and stearaldehyde.

The aldehyde is used generally in an amount at least equal in mol to 2-hydroxy-1,4-naphthoquinone as starting material, usually from 1.0 to 2.0 mol times, preferably from 1.0 to 1.4 mol times, more preferably from 1.0 to 1.3 mol times. If the amount is less than equal in mol, the yield tends to be low. On the other hand, use of an excessive amount is uneconomical. The amine of the formula $R^1NH_2$ used in the above reaction is limited to a primary amine such as an alkylamine or a cycloalkylamine. With a secondary amine or a tertially amine, formation of a 2,2'-methylene-bis-hydroxy-1,4-naphthoquinone derivative tends to be preferential. This amine may be in the form of 9as or liquid, or in an aqueous solution. $R^1$ is selected also depending upon $R^1$ of the desired compound (D). In general, a primary alkylamine such as monomethylamine, ethylamine, n-propylamine, i-propylamine, n-butylamine or t-butylamine, or a cycloalkylamine such as cyclohexylamine, may be mentioned.

The primary amine is used usually in an amount of from 0.8 to 1.5 mol times, preferably from 0.9 to 1.1 mol times, more preferably 1.0 time, relative to 2-hydroxy-1,4-naphthoquinone as starting material. If the amount of the amine is excessive or too small, the yield of the desired compound tends to be low.

As the inert organic solvent used in the above reaction, for example, an alcohol such as methanol, ethanol or propanol, a glycol ether such as methyl cellosolve, an ether such as dioxane or THF, a diol such as ethylene glycol or propylene glycol, a ketone such as MIBK, an aliphatic acid ester such as ethyl acetate or butyl acetate, an aromatic hydrocarbon such as benzene, toluene or xylene, or a halogenated hydrocarbon such as trichloroethane or tetrachloroethane, may be employed. It is usually advantageous to employ an alcohol such as methanol or ethanol to readily isolate the desired product in the form of crystals.

With respect to the reaction conditions for the above reaction, the reaction temperature is preferably not higher than 35° C., preferably from 0° to 30° C. The optimum temperature varies depending upon the solvent. However, particulary preferred is a temperature of from 15 to 25° C. If the temperature is too high, formation of a 2,2'-methylene-bis-3-hydroxy-1,4-naphthoquinone derivative tends to be prferential. If the temperature is too low, the reaction rate tends to be very low, such being impractical. The reaction is usually conducted while dropping the aldehyde at a rate not to raise the reaction temperature. The reaction time is usually from 0.5 to 5 hours including the time for the dropwise addition of the aldehyde.

The process of the present invention is conducted usually as follows.

Predetermined amounts of 2-hydroxy 1,4-naphthoquinone and the primary amine are added to a predetermined amount of the solvent to form a primary amine salt of 2-hydroxy-1,4-naphthoquinone. Then, a predetermined amount of the aldehyde is gradually added, and the reaction is conducted under stirring at a predetermined temperature for from 0.5 to 5 hours including the time for the dropwise addition of the aldehyde. Otherwise, predetermined amounts of the primary amine and the aldehyde are added to a predetermined amount of the solvent to form a Schiff base. Then, a predetermined amount of 2-hydroxy-1,4-naphthoquinone is added thereto, and the reaction is conducted under stirring at a predetermined temperature for from 0.5 to 5 hours. When the solvent is an alcohol or glycol ether, precipitated crystals are collected by filtration, and the cake thus obtained is washed with an alcohol and dried to obtain a 2-(1-alkylaminoalkyl)-3-hydroxy-1,4 naphthoquinone. If necessary, the product can be recovered also from the filtrate.

The 2-(1-alkylaminoalkyl)-3-hydroxy-1,4-naphthoquinone (D) of the present inveniton, can be subjected to deamination to obtain a 2-(1-alkenyl)-3-hydroxy-1,4-naphthoquinone (F). In this case, however, R² in the compound (D) is required to be an alkyl group having at least 2 carbon atoms, and the carbon at the α-position is required to have at least one hydrogen atoms, as shown by the following reaction scheme. This deamination reaction may be represented by the following reaction scheme, whereby the 2-(1-alkenyl)-3-hydroxy-1,4-naphthoquinone (F) is obtained via a quaternary ammonium salt (E1 as an intermediate.

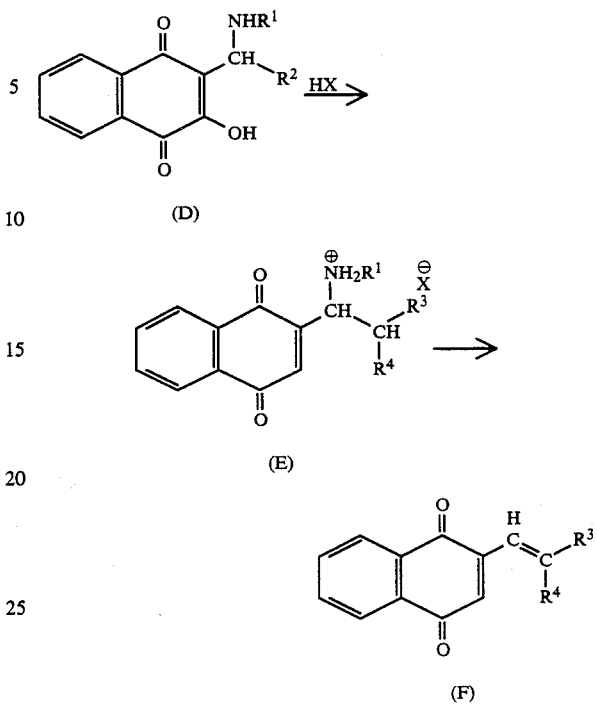

Wherein R¹ is an alkyl group or a cycloalkyl group, R² is as defined above, R³ is an alkyl group, R⁴ is a hydrogen atom or an alkyl group, and X is an acid group.

The acid used for the deamination reaction may be any acid so long as it is capable of forming a quaternary ammonium salt by the reaction with an amino group of the 2-(1-alkylaminoalkyl)-3-hydroxy-1,4-naphthoquinone (D). For example, it may be a hydrogen halide acid such as hydrochloric acid, hydrobromic acid or hydroiodic acid, or sulfuric acid.

The acid is used usually in an amount at least equal in mol to the 2-(1-alkylaminoalkyl)-3-hydroxy-1,4-naphthoquinone, preferably from 1.0 to 1.5 mol times, more preferably from 1.0 to 1.2 mol times. If the amount is too small, side reactions are likely to take place, and the yield tends to be low. On the other hand, if the amount is excessive, the reaction tends to be slow.

The solvent used for the above reaction may be an alcohol such as methanol or ethanol, a glycol ether such as methyl cellosolve or ethyl cellosolve, an aromatic hydrocarbon such as benzene, toluene or xylene, an ether such as THF or dioxane, an aliphatic acid ester such as butyl acetate, or a ketone such as methyl isobutyl ketone.

The reaction is conducted usually at a temperature of at least 75° C., preferably from 90° to 140° C. under atmospheric pressure, an elevated pressure or a spontaneous pressure. The reaction time is usually from 0.5 to 10 hours, preferably from 0.5 to 5 hours.

This deamination reaction is conducted usually as follows.

A predetermined amount of a 2-(1-alkylaminoalkyl)-3-hydroxy-1,4-naphthoquinone is added to a predetermined amount of a solvent, and a predetermined amount of an acid is added thereto at room temperature under stirring to form a quaternary ammonium salt. Then, the deamination reaction is conducted at a predetermined temperature for from 0.5 to 5 hours. Depending upon the solvent, the eliminated ammonium salt precipitates, and such an ammonium salt is collected by filtration or extracted and washed with water. Then, the reaction mixture is cooled, and precipitated crystals are collected by filtration. The cake thereby obtained is washed with an alcohol and dried to obtain crystals of a 2-(1-alkenyl)-3-hydroxy-1,4-naphthoquinone. Further, if necessary, the product can be recovered also from the filtrate. For example, the filtrate is concentrated and cooled for precipitation and recovery. For the deamination reaction, it is not necessarily required to employ an isolated 2-(1-alkylaminoalkyl)-3-hydroxy-1,4-naphthoquinone. The deamination reaction may be conducted by adding an acid to a reaction mixture containing a 2-(1-alkylaminoalkyl)-3-hydroxy-1,4-naphthoquinone obtained from 2-hydroxy-1,4-naphthoquinone, an aldehyde and a primary amine, whereby it is likewise possible to obtain crystals of a 2-(1-alkenyl) 3-hydroxy-1,4-naphthoquinone.

Now, the third aspect of the present invention will be described in detail.

Starting materials

The 2-(1 alkylaminoalkyl)-3-hydroxy 1,4-naphthoquinone used as the starting material in the present invention, can be obtained by reacting 2 hydroxy-1,4-naphthoquinone with an aliphatic aldehyde and a primary amine in an inert organic solvent, as described in detail with respect to the first aspect of the present invention.

The aldehyde to be used is a saturated aliphatic aldehyde having from 3 to 21 carbon atoms, preferably from 5 to 20 carbon atoms and having at least one hydrogen atom at the α-position. It is usual to employ a straight chain aliphatic aldehyde from the practical point of view. However, the alkyl group may be branched or cyclic, or may be substituted by an inert substituent.

Such a saturated aliphatic aldehyde may be, for example, valeraldehyde, isovaleraldehyde, pivalaldehyde, caproaldehyde, heptylaldehyde, caprylaldehyde, pelargonaldehyde, caprylaldehyde, undecylaldehyde, dodecylaldehyde (lauraldehyde), tridecylaldehyde, myristaldehyde, pentadecylaldehyde, margaraldehyde or stearaldehyde.

The amounts of these starting materials including the primary amine, the inert organic solvent and the aldehyde, and the reaction conditions, may be similar to those described with respect to the first aspect of the present invention.

The 2-(1-alkylaminoalkyl)-3-hydroxy 1,4-naphthoquinone thus obtained is not necessarily required to be isolated and may be used as it is as the starting material for the deamination step.

Deamination step

By the deamination of the 2-(1-alkylaminoalkyl)-3-hydroxy-1,4-naphthoquinone as the starting material, a 2-(1-alkenyl)-3-hydroxy-1,4-naphthoquinone can be obtained. The deamination reaction is preferably conducted by the pyrolysis in the presence of an acid.

The type and the amount of the acid, the solvent and the reaction conditions for this step may be similar to those as described with respect to the second aspect of the present invention.

The 2-(1-alkenyl)-3-hydroxy-1,4-naphthoquinone thus obtained may be isolated and used as medicines, animal drugs or agricultural chemicals. However, when it is subjected to the subsequent hydrogenation step in the present invention, the reaction solution may be used as it is for the subsequent hydrogenation step without isolating the compound from the reaction solution.

Hydrogenation step

In this hydrogenation step, it is usual to employ a hydrogenation catalyst. As such a hydrogenation catalyst, a usual metal catalyst may be used such as a palladium-carbon catalyst (Pd-C), a platinum catalyst, a rhodium carbon catalyst (Rh-C) or Raney nickel.

With respect to the reaction conditions, the reaction temperature is usually from 20° to 100° C., preferably from 30° to 70° C., and the reaction time varies depending upon the type of the catalyst or other conditions such as the pressure or the temperature, but is usually from 1 to 10 hours. The supply of hydrogen may be conducted continuously or in a batch system under atmospheric pressure or an elevated pressure.

Oxidation step

In this oxidation step, the reaction solution containing the 2-alkyl-1,3,4-trihydroxynaphthalene obtained in the preceding step is used after removing the hydrogenation catalyst. If necessary, however, the 2-alkyl-1,3,4-trihydroxynaphthalene may be isolated and then used for this step. The solvent in this case may be an inert organic solvent as used for the preparation of the starting materials, like the above cases.

As the oxidizing agent, air is usually employed. However, nitrogen may be added to control the oxygen concentration, if necessary. Further, a peroxide such as hydrogen peroxide, or an oxidizing agent such as iron chloride, may be employed.

With respect to the reaction conditions, the reaction temperature is usually from 20° to 100° C., preferably from 30° to 70° C., and the reaction time varies depending upon the amount of oxygen supplied and the efficiency of the reactor. It is advisable to determine the end of the oxidation reaction by observing the amount of absorption of oxygen.

The reaction solution after completion of the oxidation reaction, may be used by itself for the subsequent acyloxylation process. However, it is preferred to isolate the 2-alkyl-3-hydroxy-1,4-naphthoquinone from the reaction solution to separate the by-products.

The isolation may be conducted by concentrating the reaction solution from the oxidation process to precipitate the 2-alkyl-3-hydroxy-1,4-naphthoquinone, or evaporating the reaction solution to dryness and washing the solid thereby obtained with a solvent such as an alcohol.

The isolated 2-alkyl-3-hydroxy-1,4-naphthoquinone is useful by itself as medicines, animal drugs or agricultrural chemicals.

Acyloxylation step

The acyloxylation can be conducted in accordance with a usual acyloxylation method (such as a method as disclosed in Japanese Unexamined Patent Publication No. 48648/1977) by using the reaction solution obtained in the previous step or a solution or slurry of the 2-alkyl-3-hydroxy-1,4-naphthoquinone isolated in the previous step in an inert organic solvent, although it may be used without any solvent, usually in the presence of an acid such as p-toluene sulfonic acid, methane sulfonic acid or sulfuric acid, or a base such as pyridine, piperidine or triethylamine by means of an aliphatic carboxylic acid anhydride or an aliphatic carboxylic acid halide having from 2 to 6 carbon atoms.

The aliphatic carboxylic acid anhydride as an acyloxylating agent may be, for example, acetic anhydride, propionic anhydride or butylic anhydride, and the aliphatic carboxylic halide may be, for example, acetic acid chloride, propionic acid chloride or butylic acid chloride.

The acyloxylation reaction is conducted usually at a temperature of from 80° to 150° C. when an acid anhydride and an acid are employed, or generally at a temperature of not higher than 60° C., usually from 10° to 50° C. when an acid anhydride or an acid halide and a base are employed.

General process for the production

The production of the 2-alkyl-3-acyloxy-1,4-naphthoquinone of the present invention is usually conducted as follows.

A predetermined amount of 2-hydroxy-1,4-naphthoquinone is added to a predetermined amount of an inert organic solvent, and an amine such as a 40% methyl amine aqueous solution is added thereto. The mixture is heated to a predetermined temperature, and a perdetermined amount of an aliphatic aldehyde such as n-dodecylaldehyde is dropwise added. Then, the reaction is conducted under stirring for a perdetermined period of time.

A predetermined amount of an acid such as sulfuric acid is added to the reation solution containing a 2 (1-alkylaminoalkyl)-3-hydroxy-1,4-naphthoquinone thus obtained, and the temperature in the system is raised to a predetermined level for a deamination reaction to form a 2-(1 alkenyl)-3-hydroxy-1,4-naphthoquinone. Depending upon the solvent, an eliminated ammonium salt precipitates. The ammonium salt is removed by filtration or extracted with water.

The reaction solution containing the 2-(1-alkenyl)-3-hydroxy-1,4-naphthoquinone thus obtained, is cooled to a level of room temperature, and a hydrogenation catalyst such as Pd-C is added thereto. After flushing with hydrogen, the system was heated to a predetermined temperature, and the hydrogenation is conducted while supplying a hydrogen stream.

The catalyst is removed by filtration from the reaction solution thus obtained. The filtrate containing the 2-alkyl-1,3,4-trihydroxynaphthalene is oxidized at a predetermined temperature by supplying air diluted with nitrogen. The oxidation reaction solution is cooled, and precipitated crystals are collected by filtration and washed to isolate the 2-alkyl-3-hydroxy-1,4-naphthoquinone. The filtrate is concentrated and cooled to further precipitate crystals.

The isolated 2-alkyl-3-hydroxy-1,4-naphthoquinone is then added to a solvent such as o-xylene. Further, acetic anhydride as an acyloxylating agent, and p-toluene sulfonic acid as an acid, are added thereto, and the mixture is heated to a temperature of at least 100° C. and reacted for a predetermined period of time.

The reaction solution is cooled, and an acid component and a water soluble component are extracted with an aqueous alkaline solution, and the organic layer containing the product is washed with water and then evaporated to dryness to obtain a 2-alkyl-3-acyloxy-1,4-naphthoquinone as the desired product.

Otherwise, if necessary, the organic layer containing the product is concentrated and cooled, and precipitated crystals are collected by filtration and dried to obtain a 2-alkyl-3-acyloxy-1,4-naphthoquinone.

The process of the present invention basically comprises four steps. However, it is advantageous to isolate the 2-alkyl-3-hydroxy-1,4-naphthoquinone from the reaction solution obtained in the oxidation process, prior to the acyloxylation step. By this isolation, impurities can readily be removed, and it is thereby unnecessary to isolate an intermediate in other steps. Further, the desired 2-alkyl-3-acyloxy-1,4-naphthoquinone can be obtained in high purity.

Now, the present invention will be described in further detail with reference to Examples. However, it should be understood that the present invention is by no means restricted to such specific Examples. In the Examples, "%" means "% by weight" unless otherwise specified.

EXAMPLE 1

Preparation of
2-(1-methylaminobutyl)-3-hydroxy-1,4-naphthoquinone
(a)

3.50 g (20.1 mmol) of 2-hydroxy-1,4-naphthoquinone (lawson) was added to 50 ml of ethanol, and 1.60 g (20.6 mmol) of an aqueous monomethylamine solution (40% by weight) was further added thereto to obtain uniform solution of the amine salt. Then, 1.90 g (26.4 mmol) of butylaldehyde was added thereto, and the mixture was reacted at 25° C. for 1.5 hours. In about 20 minutes, crystals started to precipitate. After completion of the reaction, precipitated crystals were collected by filtration and washed with methanol to obtain 4.43 g (17.1 mmol) of crude crystals of the desired product. The yield was 85.1 mol%.

EXAMPLE 2

Preparation of
2-(1-ethylaminobutyl)-3-hydroxy-1,4-naphthoquinone
(b)

4.43 g (16.2 mmol) of crude crystals of desired product were obtained in the same manner as in Example 1 except that 1.30 g (20.2 mmol) of an aqueous ethylamine solution (70% by weight) was used instead of the aqueous methylamine solution of Example 1, and the reaction time was changed to one hour. The yield was 80.7 mol%.

EXAMPLE 3

Preparation of
2-(1-n-butylaminobutyl)-3-hydroxy-1,4-naphthoquinone (c)

5.89 g (19.6 mmol) of crude crystals of the desired product were obtained in the same manner as in Example 2 except that 1.50 g (20.5 mmol) of n-butylamine was used instead of ethylamine of Example 2. The yield was 97.3 mol%.

EXAMPLE 4

Preparation of 2-(1-methylamino-3-methyl-butyl)-3-hydroxy-1,4-naphthoquinone (d) 3.23 g (11.8 mmol) of crude crystals of the desired product were obtained in the same manner as in Example 1 except that the solvent was changed to 50 ml of methanol, 2.20 g (25.6 mmol) of isovaleraldehyde was used instead of butylaldehyde, and the reaction time was changed to 3 hours. The yield was 58.9 mol%.

EXAMPLE 5

Preparation of 2-(1-cyclohexylamino-decanyl) 3-hydroxy-1,4-naphthoquinone (e) 6.80 g (16.5 mmol) of crude crystals of the desired product were obtained in the same manner as in Example 4 except that the aldehyde was changed to 3.80 g (24.4 mmol) of caproaldehyde, and the amine was changed to 2.00 g (20.2 mmol) of cyclohexylamine. The yield was 82.3 mol%.

EXAMPLE 6

Preparation of 2 (1-i-propylaminododecyl)-3-hydroxy-1,4-naphthoquinone (g)

6.00 g (34.5 mmol) of lawson and 2.06 g (34.5 mmol) of i-propylamine were added to 100 ml of methanol, and 7.62 g (41.3 mmol) of n-dodecylaldehyde was added thereto under water bath (27° C.). The reaction was conducted for three hours. After completion of the reaction, precipitated crystals were collected by filtration and washed with methanol to obtain 9.76 g of 2-(1-i-propylaminodecyl)-3-hydroxy-1,4-naphthoquinone. The yield was 70 mol%.

Further, the filtrate was analyzed by HPLC (high performance liquid chromatography), whereby 0.21 g of unreacted lawson and 2.72 g of the desired product were confirmed in the filtrate. If the desired product in this filtrate is added, the total amount is 12.48 g (31.2 mmol), and the overall yield is 90.4 mol%.

EXAMPLE 7

Preparation of 2-(1-n butylaminododecyl)-3-hydroxy-1,4-naphthoquinone (h)

6.72 g (16.2 mmol) of 2 (1-n-butylaminododecyl)-3-hydroxy-1,4-naphthoquinone was obtained in the same manner as in Example 6 except that 2.55 g (34.5 mmol) of n-butylamine was used instead of i-propylamine. Further, as a result of the analysis of the filtrate by HPLC, it was confirmed that the unreacted lawson was 0.11 g, and the desired product was 6.57 g. The total amount was 3.29 g (32.1 mmol), and the yield was 93.0 mol%.

EXAMPLE 8

Preparation of 2-(1-t-butylaminododecyl)-3-hydroxy-1,4-naphthoquinone (i)

5.67 g (13.7 mmol) of 2-(1-t butylaminododecyl)-3-hydroxy-1,4-naphthoquinone was obtained in the same manner as in Example 6 except that 2.55 g (34.5 mmol) of t-butylamine was used as the amine. Further, from the analysis of the filtrate by HPLC, it was confirmed that unreacted lawson was 2.62 g, and the desired product was 1.49 g. The total amount was 7.16 g (17.3 mmol), and the yield was 50.1 mol%.

EXAMPLE 9

Preparation of 2-(1-methylaminododecyl)-3-hydroxy-1,4-naphthoquinone (f)

19.7 g (113 mmol) of lawson, 8.77 g (113 mmol) of a 40% methylamine aqueous solution, 300 ml of methanol and 20.3 g of water were stirred at room temperature, and 25.0 g (135.6 mmol) of n-dodecylaldehyde was added thereto. The mixture was reacted for 3 hours. Precipitated crystals were collected by filtration and washed with methanol to obtain 33.9 g (91.4 mmol) (80.9 mol%) of crude crystals of 2-(1-methylaminododecyl)-3-hydroxy-1,4-naphthoquinone. Further, the filtrate was analyzed by HPLC, and it was confirmed that the desired product was 3.28 g (8.84 mmol) and unreacted lawson was 1.45 g (8.33 mmol).

EXAMPLE 10

The reaction was conducted in the same manner as in Example 1 except that THF was used instead of ethanol as the sovlent and 4.44 g (24.1 mmol) of n dodecylaldehyde was used instead of butylaldehyde. A part of the uniform solution thus obtained was sampled and analyzed by HPLC, whereby 8.22 g (19.9 mmol) of 2-(1-methylaminododecyl)-3-hydroxy-1,4-naphthoquinone was confirmed. The yield was 99.0 mol%.

The IR (number of stretching vibrations of C=O: $\nu$, $cm^{-1}$), NMR and melting point (m.p.) of the compound thus obtained are shown in Table 1, and the results of the elemental analysis are shown in Table 2.

TABLE 1

| | I.R. | N.M.R.(ppm) (CDCl$_3$) | m.p. |
|---|---|---|---|
| a | $\nu_{c=0}$ 1668 | 0.85(t.3H) 1.25–1.44(m.2H) 1.54–1.93 and 1.93–2.15(m.2H) 2.76(s.3H) 4.73–4.92(m.1H) 7.51–7.78(m.2H) 7.97–8.18(m.2H) 8.63–9.24(bs.1H) 10.48–11.04(bs.1H) | 153° C. Decomposed |
| b | $\nu_{c=0}$ 1665 | 0.89(t.3H) 1.30(t.3H) 1.28–1.57(m.2H) 1.73–1.97(m.1H) 1.97–2.25(m.1H) 2.99–3.34(m.2H) 4.82–5.08(m.1H) 7.52–7.80(m.2H) 8.00–8.20(m.2H) 8.69–9.18(bs.1H) 10.50–10.98(bs.1H) | 163° C. Decomposed |
| c | $\nu_{c=0}$ 1680 | 0.88(t.3H) 1.35(t.3H) 1.48–1.73(m.6H) 1.73–1.94 and 1.94–2.14(m.2H) 2.89–3.06 and 3.06–3.22(m.2H) 4.78–4.95(m.1H) 7.51–7.76(m.2H) 7.98–8.18(m.2H) 8.70–9.05(bs.1H) 10.50–11.02(bs.1H) | 167° C. Decomposed |
| d | $\nu_{c=0}$ 1672 | 0.87(d.3H) 1.03(d.3H) 1.48–1.73(m.2H) 1.91–2.20(m.2H) 2.78(s.3H) 4.79–5.00(m.1H) 7.53–7.78(m.2H) 7.98–8.21(m.2H) 8.43–9.00(m.1H) 10.57–11.00(m.1H) | 159° C. Decomposed |
| e | $\nu_{c=0}$ 1665 1665 | 0.83(t.3H) 0.90–2.60(m.26H) 2.80–3.28(m.1H) 4.80–5.35(m.1H) 7.60–7.92(m.2H) 8.06–8.38(m.2H) 9.40–10.18(bs.1H) 10.70–11.24(bs.1H) | 149° C. |
| f | $\nu_{c=0}$ 1665 | 1.85(t.3H) 1.01–1.60(m.18H) 1.60–1.95 and 1.95–2.20(m.2H) 2.78(s.3H) 4.80–5.02(m.1H) 7.58–7.80(m.2H) 8.00–8.22(m.2H) 8.70–9.12(bs.1H) 10.54–11.03(bs.1H) | 87–91° C. |
| g | $\nu_{c=0}$ 1670 | 0.89(t.3H) 1.00–1.78(m.18H) 1.40(d.3H) 1.61(d.3H) 1.78–2.45(m.2H) 3.22–3.75(m.1H) 4.88–5.36(m.1H) | 141° C. Decomposed |

TABLE 1-continued

| | I.R. | N.M.R.(ppm) (CDCl₃) | m.p. |
|---|---|---|---|
| | | 7.62–7.94(m.2H) 8.08–8.38(m.2H) 8.52–9.04(bs.1H) 10.48–10.95(bs.1H) | |
| h | $v_{c=o}$ 1663 | 0.83(t.3H) 1.00–2.42(m.24H) 2.84–3.42(m.2H) 4.74–5.27(m.1H) 7.61–7.94(m.2H) 8.08–8.43(m.2H) 8.80–9.30(bs.1H) 10.52–11.08(bs.1H) | 130–132° C. |
| i | $v_{c=o}$ 1668 | 0.86(t.3H) 0.98–1.85(m.18H) 1.50(s.9H) 1.85–2.40(m.2H) 4.81–5.30(m.1H) 7.58–8.60(m.2H) 8.02–8.33(m.2H) 8.78–9.28(bs.1H) 10.60–11.05(bs.1H) | 139–141° C. |

TABLE 2

| | R²/R¹ | Molecular weight | Elemental analysis Measured values (Calculated values) | | |
|---|---|---|---|---|---|
| | | | C | H | N |
| a | n-Pr/Me | 259.308 | 69.71 (69.48) | 6.83 (6.61) | 5.44 (5.40) |
| b | n-Pr/Et | 273.335 | 70.55 (70.31) | 6.89 (7.01) | 5.01 (5.12) |
| c | n-Pr/n-Bu | 301.389 | 71.99 (71.74) | 7.80 (7.69) | 4.72 (4.65) |
| d | i-Bu/Me | 273.335 | 69.98 (70.31) | 6.79 (7.01) | 5.22 (5.12) |
| e | n-C₉H₁₉/ | 411.590 | 75.81 (75.87) | 9.25 (9.06) | 3.33 (3.40) |
| f | n-C₁₁H₂₃/Me | 371.524 | 74.53 (74.36) | 8.99 (8.95) | 3.92 (3.77) |
| g | n-C₁₁H₂₃/i-Pr | 399.579 | 75.14 (75.15) | 9.01 (9.33) | 3.70 (3.51) |
| h | n-C₁₁H₂₃/n-Bu | 413.606 | 75.17 (75.50) | 9.32 (9.50) | 3.50 (3.39) |
| i | n-C₁₁H₂₃/t-Bu | 413.606 | 75.74 (75.50) | 9.28 (9.50) | 3.51 (3.39) |

EXAMPLE 11

Preparation of 2-(1-dodecyl)-3-hydroxy-1,4-naphthoquinone 3.34 g (8.09 mmol) of 2-(1-n butylaminododecyl)-3-hydroxy-1,4-naphthoquinone (h) obtained in Example 7 was added to 30 ml of methyl cellosolve, and 0.92 g (8.92 mmol) of sulfuric acid was added thereto under stirring at room temperature to obtain a uniform solution of the sulfate. The solution was heated to 120° C., and the deamination reaction was conducted for one hour. After completion of the reaction, the reaction solution thus obtained was cooled, and precipitated crystals were collected by filtration and thoroughly washed with methanol to obtain 2.23 g (6.56 mmol) (81.1 mol%) of crystals of 2-(1-dodecenyl)-3-hydroxy-1,4-naphthoquinone was obtained. Further, the filtrate was analyzed by HPLC, whereby 0.11 g (0.32 mmol) (4.0 mol%) of the product was confirmed.

EXAMPLE 12

2.54 g (7.47 mmol) (92.9 mol%) of crystals of 2 (1-dodecenyl)-3-hydroxy-1,4-naphthoquinone was obtained in the same manner as in Example 11 except that 3.32 g (8.04 mmol) of 2-(1-t-butylaminododecyl)-3-hydroxy-1,4-naphthoquinone (i) obtained in Example 8 was used instead of (h). Further, the filtrate was analyzed by HPLC, whereby 145 mg (0.43 mmol)(5.3 mol%) of the product was confirmed.

EXAMPLE 13

Preparation of 2-(1-butenyl)-3 hydroxy-1,4-naphthoquinone 3.00 g (9.97 mmol) of 2-(1-n-butylaminobutyl)-3-hydroxy-1,4-naphthoquinone (c) obtained in Example 3 was added to 50 ml of methyl cellosolve, and 1.15 g (11.0 mmol) of concentrated hydrochloric acid was added thereto under stirring at room temperature to form the hydrochloride. This reaction solution was heated to 120° C. and maintained for one hour for the deamination reaction. After completion of the reaction, the reaction solution was concentrated under reduced pressure, and the oil thereby obtained was separated and purified by silica gel column chromatography (ethyl acetate/n-hexane = ¼) to obtain 1.85 g (8.11 mmol) (81.4 mol%) of crystals of 2-(1-butenyl)-3-hydroxy-1,4-naphthoquinone.

EXAMPLE 14

Preparation of 2-(3-methyl-1-butenyl)-3-hydroxy-1,4-naphthoquinone 1.30 g (5.37 mmol) (73.3 mol%) of crystals of 2-(3-hydroxy-1,4-naphthoquinone were obtained in the same manner as in Example 11 except that 2.00 g (7.33 mmol) of 2-(1-methylamino-3-methylbutyl)-3-hydroxy-1,4-naphthoquinone (d) obtained in Example 4 was used instead of 2-(1-butylaminobutyl)-3-hydroxy-1,4-naphthoquinone in Example 11 and the amount of hydrochloric acid was changed to 0.80 g (7.67 mmol).

EXAMPLE 15

Into a 30 ml glass autoclave, 1.00 g (2.67 mmol) of 2-(1-methylaminododecyl)-3-hydroxy-1,4-naphthoquinone, 305.6 mg (1.1 mmol times relative to the starting material) of concentrated sulfuric acid and 20 ml of xylene were charged, then heated to 120° C. under stirring and maintained at that temperature for one hour. The mixture was left to cool and then extracted with a benzene/water system. The organic layer was dried over sodium sulfate, and the solvent was distilled off. The residue was recrystallized from methanol to obtain 734.6 mg of 2-(1-dodecenyl)-3-hydroxy-1,4-naphthoquinone. Further, the filtrate of the recrystallization was analyzed by HPLC, whereby it was confirmed that the filtrate contained 12.4 mg of 2-hydroxy-1,4-naphthoquinone, 0.7 mg of the starting material and 15.5 mg of the desired product. The yield, etc. are shown in Table 3.

EXAMPLES 16 TO 18

The operation was conducted in the same manner as in Example 13 except that the solvent was changed to those identified in Table 3. However, the extraction was conducted with an ethyl acetate/water system. The yields thus obtained are shown in Table 3.

TABLE 3

| Example | Solvent | Yield (%) |
|---|---|---|
| 15 | Xylene | 81.6 |
| 16 | Dioxane | 80.5 |
| 17 | Ethyl acetate | 84.8 |
| 18 | Methyl i-butyl ketone | 83.2 |

EXAMPLE 19

Preparation of
2-(1-dodecenyl)-3-hydroxy-1,4-naphthoquinone

In 70 ml of butyl acetate, 3.52 g (20.2 mmol) of 2-hydroxy 1,4 naphthoquinone, 1.60 g (20.6 mmol) of methylamine (40%) and 4.40 g (23.9 mmol) of n-dodecylaldehyde were reacted at room temperature for two hours. The reaction solution thereby obtained was analyzed by HPLC, and it was confirmed that the reaction solution contained 7.28 g (19.6 mmol) of 2-(1-methylaminododecyl)-3-hydroxy-1,4-naphthoquinone. To the reaction mixture, 2.08 g (20.2 mmol) of concentrated sulfuric acid was gradually added to obtain a solution of the sulfate (a uniform solution was obtained at 50° C). Then, the deamination reaction was conducted under reflux for one hour.

After completion of the reaction, the reaction solution was cooled, and precipitated crystals were collected by filtration and washed with methanol to obtain 5.13 g (15.1 mmol) (74.8 mol%) of crystals of 2-(1-dodecenyl)-3-hydroxy-1,4-naphthoquinone. Further, the filtrate was analyzed by HPLC, whereby 0.70 g (2.06 mmol) (10.2 mol%) of the product was confirmed.

Thus, by this reaction, 2-(1-dodecenyl)-3-hydroxy-1,4-naphthoquinone was prepared from 2-hydroxy-1,4-naphthoquinone in a yield of 85.0%.

EXAMPLE 20

Preparation of
2-(1-dodecenyl)-3-hydroxy-1,4-naphthoquinone

In 400 ml of toluene, 22.80 g (131.0 mmol) of 2-hydroxy-1,4-naphthoquinone and 9.60 g (131.5 mmol) of butylamine were reacted to form an amine salt of lawson. Then, while maintaining the reaction temperature at a level of from 20° to 25° C., 26.1 g (141.8 mmol) of dodecylaldehyde was dropwise added thereto over a period of about 20 minutes. After completion of the dropwise addition, the reaction was continued for further 30 minutes.

The reaction solution thus obtained was analyzed by HPLC, and it was confirmed that the reaction solution contained 52.00 g (128.4 mmol) of 2-(1-butylaminododecyl)-3-hydroxy-1,4-naphthoquinone. (Yield: 98.0 mol%)

Then, to this reaction mixture, 13.90 g (134.7 mmol) of concentrated sulfuric acid was gradually added to obtain a solution of the sulfate. Then, the deamination reaction was conducted under reflux with toluene (110° C.) for 90 minutes.

After completion of the reaction, when the liquid temperature became about 80° C., 40 ml of water was added, and the amine salt of sulfuric acid formed as a by-product was extracted, and the mixture was left to stand still. The toluene layer was concentrated to dryness, and precipitated crystals were washed with 300 ml of methanol and subjected to filtration to obtain 40.9 g (120.3 mmol) (91.8 mol%) of crystals of 2-(1-dodecenyl)-3-hydroxy-1,4-naphthoquinone. Further, from the analysis by HPLC, it was confirmed that the filtrate contained 0.66 g (1.9 mmol) (1.5 mol%) of the product.

Thus, by this reaction, 2 (1-dodecenyl)-3-hydroxy-1,4-naphthoquinone was prepared from 2-hydroxy-1,4 naphthoquinone in a yield of 93.3 mol%.

COMPARATIVE EXAMPLE 1

2.5 g (14.4 mmol) of 2-hydroxy-1,4-naphthoquinone was added to 50 ml of acetic acid, and 5.4 g (2.03 mol times relative to 2-hydroxy-1,4-naphthoquinone) of n-dodecylaldehyde and 7.5 g (1.4 mol times relative to 2-hydroxy 1,4-naphthoquinone) of concentrated hydrochloric acid were added as catalyst, and the reaction was conducted at 85° C. for two hours. The reaction solution thus obtained was cooled to about 5° C., whereby no crystal precipitated. Therefore, the reaction solution was poured into 300 ml of water and extracted with 200 ml of benzene. This organic layer was washed twice with 150 ml of a 1% sodium carbonate aqueous solution and once with 150 ml of water and dried over anhydrous sodium sulfate. Benzene was distilled off, and the obtained oil layer was purified by silica gel column chromatography to obtain 1.97 g of 2-(1-dodecenyl)-3 hydroxy-1,4-naphthoquinone. The yield was 40.2 mol%.

EXAMPLE 21

Preparation of 2-(1-methylaminododecyl)
3-hydroxy-1,4-naphthoquinone

Into a 1 l four necked flask, 550 ml of ethyl cellosolve was charged. While gently stirring it with a stirrer, 38.0 g (218 mmol) of 2-hydroxy-1,4-naphthoquinone was added thereto. Then, 17.40 g (224 mmol) of a 40% methylamine aqueous solution was added thereto. While maintaining the temperature of the liquid in the flask to a level of 22° C. in a water bath, a mixture comprising 48.00 g (260 mmol) of n-dodecylaldehyde and 50 ml of ethyl cellosolve, was dropwise added over a period of 30 minutes by means of a dropping funnel. Then, the mixture was reacted for two hours.

Deamination step

To this reaction solution, 24.00 g (233 mmol) of 95% sulfuric acid was added, and the temperature in the reaction system was raised to 120° C. Then, the deamination reaction by thermal decomposition was conducted for 15 minutes.

Hydrogenation step

The reaction solution from the above deamination reaction was cooled to 30° C., and 2.00 g of Pd-C containing 50% of water was added thereto as a hydrogenation catalyst. After flushing the reaction system with hydrogen, the temperature in the system was raised to 55° C., and hydrogenation was conducted for 5 hours under a hydrogen stream. After completion of the hydrogenation, the system was flushed with nitrogen, and the catalyst was separated by filtration.

Oxidation step

The filtrate from the hydrogenation reaction from which the catalyst was removed by filtration, was maintained at a temperature of from 50° to 55° C., and air diluted with nitrogen to an oxygen concentration of 10%, was blown into the reaction solution at a rate of 800 ml/min, and the reaction was conducted under stirring for 6 hours. After completion of the reaction, the reaction solution was cooled to 8° C. to precipitate crystals. The precipitated crystals were collected by filtration and washed with 60 ml of cold methanol and dried to obtain 43.0 g of 2-dodecyl-3-hydroxy-1,4-naphthoquinone.

Acyloxylation step

Into a 1 l four necked flask, 400 ml of o-xylene was charged, and 41.0 g (119.7 mmol) of 2-dodecyl-3-hydroxy-1,4-naphthoquinone obtained in the above step, 37.0 g (362.4 mmol) of acetic anhydride and 1.03 g (5.4 mmol) of p-toluene sulfonic acid were added under stirring. Then, the temperature was raised to 120° C. over a period of 40 minutes, and the reaction was conducted at that temperature for 4.5 hour.

After completion of the reaction, the reaction solution was cooled to 30° C., and the acid component and the water-soluble component were extracted with a 15% sodium carbonate aqueous solution, and the organic layer was further washed with 250 ml of water. This organic layer was evaporated to dryness, and crystals thereby obtained were dried to obtain 46.45 g (120.8 mmol) of crystals of 2-dodecyl-3-acetoxy-1,4-naphthoquinone.

The yield relative to the 2 hydroxy-1,4-naphthoquinone used for the preparation of 2-(1-methylaminododecyl)-3-hydroxy-1,4-naphthoquinone, was 56.7 mol%. Further, yield relative to the starting material 2 (1-methylaminododecyl) 3-hydroxy 1,4-naphthoquinone was 61.0 mol%.

EXAMPLE 22

Preparation of 2-(1-methylaminododecyl)-3-hydroxy-1,4-naphthoquinone

In 200 ml of butyl acetate, 7.35 g (42.2 mmol) of 2-hydroxy-1,4-naphthoquinone, 3.28 g (42.3 mmol) of a 40% of methylamine aqueous solution and 9.33 g (50.7 mmol) of n-dodecylaldehyde were reacted at room temperature for two hours.

The reaction solution thereby obtained was analyzed by HPLC, and it was confirmed that the reaction solution contained 15.50 g (41.8 mmol) of 2-(1-methylaminododecyl)-3-hydroxy-1,4-naphthoquinone.

Deamination step

To the above reaction solution, 4.70 g (45.5 mmol) of 95% sulfuric acid was gradually added to obtain a uniform solution of the sulfate at 50° C. Then, the solution was heated to 120° C., and the deamination reaction by thermal decomposition was conducted for one hour.

Hydrogenation step

The reaction solution containing 2-(1 dodecenyl)-3-hydroxy-1,4 naphthoquinone obtained in the deamination step, was cooled to 30° C., and 0.50 g of a Pd-C catalyst containing 50% of water, was added thereto. Then, the hydrogenation was conducted for three hours at 50° C. under a hydrogen stream.

After completion of the hydrogenation, the reaction system was flushed with nitrogen, and the catalyst was separated by filtration to obtain a filtrate containing 2-dodecyl-1,3,4-trihydroxynaphthalene.

Oxidation step

The filtrate obtained in the preceding step was maintained at 50° C., and air diluted with nitrogen to an oxygen concentration of 10%, was blown thereinto at a rate of 400 ml/min, and the reaction was continued for 4 hours. Then, the reaction solution was cooled to 10° C., and precipitated crystals were collected by filtration. The crystals thus obtained were washed with cold methanol, and dried to obtain 9.23 g (27.0 mmol) of crystals of 2-dodecyl-3-hydroxy-1,4-naphthoquinone.

The filtrate from which the crystals were separated by filtration, was concentrated to 60 ml and cooled, and precipitated crystals were collected by filtration, washed and dried to obtain 1.62 g (4.7 mmol) of crystals of 2-dodecyl-3-hydroxy-1,4-naphthoquinone additionally.

Acyloxylation step 4.67 g (13.6 mmol) of crystals of 2-dodecyl-3-hydroxy-1,4-naphthoquinone obtained in the preceding step were added to 50 ml of o-xylene, and 3.00 g (29.4 mmol) of acetic anhydride and 0.40 g of p-toluene sulfonic acid were further added thereto. The mixture was reacted at 120° C. for 4 hours.

This reaction solution was cooled to 30° C., and the acid component and the water-soluble component were extracted with 30 ml of a 10% sodium carbonate aqueous solution, and the organic layer was further washed with 30 ml of water. This organic layer was evaporated to dryness to obtain 5.26 g (13.3 mmol) of crystals of 2-dodecyl-3-acetoxy-1,4-naphthoquinone having a purity of 97.2%.

The yield relative to 2 hydroxy-1,4-naphthoquinone used for the preparation of 2 (1 methylaminododecyl)-3-hydroxy-1,4-naphthoquinone, was 73.5 mol%. Further, the yield relative to the starting material 2-(1-methylaminododecyl)-1,4-naphthoquinone, was 74.2 mol%.

EXAMPLE 23

Preparation of 2-(1-methylaminododecyl)-3-hydroxy-1,4-naphthoquinone

In 400 ml of toluene, 22.80 g (131.0 mmol) of 2-precipitated hydroxy-1,4-naphthoquinone, 9.60 g (131.5 mmol) of butylamine and 26.10 g (141.8 mmol) of n-dodecylaldehyde were reacted at room temperature for two hours.

The reaction solution thereby obtained was analyzed by HPLC, and it was confirmed that the reaction solution contained 52.00 g (128.4 mmol) of 2-(1-butylaminododecyl)-3-hydroxy-1,4-naphthoquinone.

Deamination step

To the above reaction solution, 13.90 g (134.7 mmol) of 95% sulfuric acid was gradually added to obtain a uniform solution of the sulfate at 50° C. Then, the temperature was raised to 110° C., and the deamination reaction by thermal decomposition was conducted for 90 minutes. When this reaction solution became 80° C., 40 ml of water was added thereto, and the amine salt of sulfuric acid formed as a by-product was extracted under stirring, and the reaction solution was left to stand still for separation.

Hydrogenation step

The reaction solution containing 2-(1-dodecenyl)-3-hydroxy-1,4-naphthoquinone obtained in the deamination step, was cooled to 30° C., and 2.00 g of a Pd-C catalyst containing 50% of water, was added thereto. Then, hydrogenation was conducted at 60° C. for 3 hours under a hydrogen pressure of 3 kg/cm$^2$ G. After completion of the hydrogenation, the reaction system was flushed with nitrogen, and the catalyst was separated by filtration to obtain a filtrate containing 2-dodecyl-1,3,4-trihydroxynaphthalene.

Oxidation step

The filtrate obtained in the preceding step was maintained at 50° C., and air diluted with nitrogen to an oxygen concentration of 10%, was blown thereinto at a rate of 800 ml/min, and the reaction was continued for 4 hours. Then, the reaction solution was concentrated under reduced pressure to a volume of 150 ml. Then, the reaction solution was cooled to 15° C., and precipitated crystals were collected by filtration. The crystals thus obtained were washed with cold toluene and dried to obtain 36.80 g (purity: 99.0%) (106.5 mmol) of crystals of 2-dodecyl-3-hydroxy-1,4-naphthoquinone.

The filtrate from which crystals were separated by filtration, was analyzed by HPLC, and it was confirmed that the filtrate contained 2.42 g (7.1 mmol) of 2-dodecyl-3-hydroxy-1,4-naphthoquinone.

Acyloxylation step 36.80 g (106.5 mmol) of 2-dodecyl 3-hydroxy 1,4-naphthoquinone obtained in the preceding step, was added to 50 ml of toluene, and 32.40 g (317.6 mmol) of acetic anhydride and 0.40 g of p-toluene sulfonic acid were further added thereto. The mixture was reacted at 110° C. for one hour.

This reaction solution was cooled to 30° C., and the acid component and the water-soluble component were extracted by adding 200 ml of a 20% sodium carbonate aqueous solution and 100 ml of toluene. Further, the organic layer was washed with 200 ml of water. This organic layer was evaporated to dryness to obtain 41.44 g (104.9 mmol) of crystals of 2-dodecyl-3 acetoxy-1,4-naphthoquinone having a purity of 97.2%.

The yield relative to 2-hydroxy-1,4-naphthoquinone used for the preparation of 2-(1 butylaminododecyl)-3-hydroxy-1,4-naphthoquinone, was 80.1 mol%. Further, the yield relative to the starting material 2-(1-butylaminododecyl)-1,4-naphthoquinone, was 81.7 mmol%.

The 2-(1-alkylaminoalkyl)-3-hydroxy-1,4-naphthoquinone obtained by the present invention is considered to have biological activities by itself. However, it can be led by deamination to a 2-(1-alkenyl)-3-hydroxy-1,4-naphthoquinone, and a 2-alkyl-3-hydroxy-1,4-naphthoquinone, which are useful as intermediates for medicines or agricultural chemicals.

The process for the preparation of a 2 alkyl-3-acyloxy-1,4-naphthoquinone according to the present invention employs as its starting material a 2-(1-alkylaminoalkyl)-3-hydroxy-1,4-naphthoquinone, whereby an expensive starting material such as an organo metal compoumd is not required, and a product of a high purity can readily be produced in good yield by using an inexpensive material. Therefore as compared with the conventional processes, it is extremely useful as an industrial process.

According to the process of the present invention, the intermediate can be isolated and purified in an intermediate step by suitably selecting the solvent used in the step whereby impurities can readily be separated.

I claim:

1. A 2-(1-alkylaminoalkyl)-3-hydroxy-1,4-naphthoquinone of the formula:

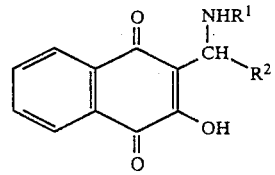

wherein $R^1$ is a $C_1-C_6$ alkyl or cycloalkyl group, and $R^2$ is an alkyl group having 3 to 20 carbon atoms.

2. The compound of claim 1 wherein $R^1$ is methyl and $R^2$ is n-propyl.

3. The compound of claim 1 wherein $R^1$ is ethyl and $R^2$ is n-propyl.

4. The compound of claim 1 wherein $R^1$ is n-butyl and $R^2$ is n-propyl.

5. The compound of claim 1 wherein $R^1$ is methyl and $R^2$ is i-butyl.

6. The compound of claim 1 wherein $R^1$ is cyclohexyl and $R^2$ is n-$C_9H_{19}$.

7. The compound of claim 1 wherein $R^1$ is methyl and $R^2$ is n-$C_{11}H_{23}$.

8. The compound of claim 1 wherein $R^1$ is i-propyl and $R^2$ is n-$C_{11}H_{23}$.

9. The compound of claim 1 wherein $R^1$ is n-butyl and $R^2$ is n-$C_{11}H_{23}$.

10. The compound of claim 1 wherein $R^1$ is t-butyl and $R^2$ is n-$C_{11}H_{23}$.

* * * * *